US012584908B2

(12) United States Patent
Kuwahara

(10) Patent No.: US 12,584,908 B2
(45) Date of Patent: Mar. 24, 2026

(54) IMMUNOASSAY METHOD AND IMMUNOASSAY APPARATUS

(71) Applicant: Denka Company Limited, Tokyo (JP)

(72) Inventor: Miwa Kuwahara, Niigata (JP)

(73) Assignee: Denka Company Limited, Tokyo (JP)

( * ) Notice: Subject to any disclaimer, the term of this patent is extended or adjusted under 35 U.S.C. 154(b) by 908 days.

(21) Appl. No.: 17/784,417

(22) PCT Filed: Dec. 11, 2020

(86) PCT No.: PCT/JP2020/046257
    § 371 (c)(1),
    (2) Date: Jun. 10, 2022

(87) PCT Pub. No.: WO2021/117862
    PCT Pub. Date: Jun. 17, 2021

(65) Prior Publication Data
    US 2023/0003724 A1     Jan. 5, 2023

(30) Foreign Application Priority Data

Dec. 12, 2019    (JP) ................................. 2019-224865

(51) Int. Cl.
    *C07K 16/10*        (2006.01)
    *G01N 33/543*       (2006.01)
    *G01N 33/569*       (2006.01)
(52) U.S. Cl.
    CPC ....... *G01N 33/543* (2013.01); *C07K 16/1027* (2013.01); *G01N 33/569* (2013.01)
(58) Field of Classification Search
    CPC .............. G01N 33/543; G01N 33/569; G01N 33/54387; G01N 33/56983; G01N 2333/135; G01N 33/54393; C07K 16/1027
    See application file for complete search history.

(56) References Cited

U.S. PATENT DOCUMENTS

2016/0139125  A1     5/2016  Kosaka et al.

FOREIGN PATENT DOCUMENTS

| CN | 109459567 | A | 3/2019 |
| CN | 105753981 | B | 10/2019 |
| EP | 0 368 624 | A2 | 5/1990 |
| EP | 2 145 899 | A1 | 1/2010 |
| EP | 3 012 633 | A1 | 4/2016 |
| EP | 3 872 491 | A1 | 9/2021 |
| JP | 61189454 | A * | 8/1986 |
| JP | 11-153600 | * | 6/1999 |
| JP | 11-153600 | A | 6/1999 |
| JP | 2000-310639 | A | 11/2000 |
| JP | 2005-300401 | * | 10/2005 |
| JP | 2005-300401 | A | 10/2005 |
| JP | 6454274 | B2 | 2/2019 |
| WO | WO 2014/203988 | * | 12/2014 |
| WO | WO-2014/203988 | A1 | 12/2014 |
| WO | WO-2020/180553 | A1 | 9/2020 |

OTHER PUBLICATIONS

Supplementary European Search Report dated May 19, 2023 in EP 20900363.1.
Office Action with Search Report dated Oct. 19, 2024 in CN 202080085881.5.
Office Action issued in connection with EP Appl. No. 20900363.1 dated Feb. 9, 2024.
Trinh Thi Thuy Tien Et et al., "Development of a Rapid Fluorescent Immunochromatographic Test to Detect Respiratory Syncytial Virus", International Journal of Molecular Sciences 2018, 19, 3013.
Trinh Thi Thuy Tien et al., "Development of a Rapid Fluorescent Immunochromatographic Test to Detect Respiratory Syncytial Virus", International Journal of Molecular Sciences 2018, 19, 3013.
Office Action and Search Report dated Jul. 2, 2024 in TW 109143829.
Paulini et al., "Development of a prototype immunochromatographic test for rapid diagnosis of respiratory adenovirus infection," The Brazilian Journal of Infectious Diseases, Jun. 15, 2017, 21(5):500-506.
International Search Report dated Mar. 2, 2021 in PCT/JP2020/046257.

* cited by examiner

*Primary Examiner* — Kimberly Ballard
*Assistant Examiner* — Stacey N Macfarlane
(74) *Attorney, Agent, or Firm* — Foley & Lardner LLP

(57) ABSTRACT

Provided are a highly-sensitive antibody and a test reagent using the antibody.
A method for detecting an analyte according to an immunoassay method, using a carrier on which an antigen, an antibody or an antigen-binding fragment thereof is immobilized, wherein
    the analyte is detected with increasing detection sensitivity by using a carrier to which an antigen, an antibody or an antigen-binding fragment thereof was immobilized by adding disaccharide and sugar alcohol to a solution comprising an antigen, an antibody or an antigen-binding fragment thereof.

5 Claims, No Drawings

IMMUNOASSAY METHOD AND IMMUNOASSAY APPARATUS

CROSS-REFERENCE TO RELATED APPLICATIONS

This application is the U.S. National Stage of PCT/JP2020/046257, filed Dec. 11, 2020, which claims priority to JP 2019-224865, filed Dec. 12, 2019.

TECHNICAL FIELD

The present invention relates to an immunoassay method and an immunoassay apparatus.

BACKGROUND ART

At present, test reagents using various types of antibodies are commercially available. However, for example, in a case where an RS virus has been detected using a conventional RS virus test reagent, sensitivity has not been sufficient (Patent Literature 1).

CITATION LIST

Patent Literature

Patent Literature 1: Japanese Patent No. 6454274

SUMMARY OF INVENTION

Technical Problem

Under the above-described current circumstances, it is an object of the present invention to provide a highly-sensitive immunoassay method, and a test reagent using the same.

Solution to Problem

The present inventors have found that, upon immobilization of an antigen, an antibody or an antigen-binding fragment thereof, detection sensitivity can be improved by addition of disaccharide and sugar alcohol, thereby completing the present invention.

Specifically, the present invention is as follows.

[1]

A method for detecting an analyte according to an immunoassay method, using a carrier on which an antigen, an antibody or an antigen-binding fragment thereof is immobilized, wherein the analyte is detected with increasing detection sensitivity by using a carrier to which an antigen, an antibody or an antigen-binding fragment thereof was immobilized by adding disaccharide and sugar alcohol to a solution comprising an antigen, an antibody or an antigen-binding fragment thereof.

[2] The method according to the above [1], wherein 1% to 4% (w/v) of the disaccharide and 0.5% to 4% (w/v) of the sugar alcohol are added to the solution comprising an antigen, an antibody or an antigen-binding fragment thereof, so that the antigen, the antibody or an antigen-binding fragment thereof are immobilized on the carrier.

[3] The method according to the above [1] or [2], wherein the disaccharide is trehalose or maltose.

[4] The method according to any one of the above [1] to [3], wherein the sugar alcohol is mannitol or sorbitol.

[5] The method according to any one of the above [1] to [4], which is immunochromatography.

[6] The method according to any one of the above [1] to [5], wherein the antibody or an antigen-binding fragment thereof is an anti-RS virus N protein antibody or an antigen-binding fragment thereof.

[7] A detection reagent with increased detection sensitivity, in which an antigen, an antibody or an antigen-binding fragment thereof are immobilized, wherein disaccharide and sugar alcohol are comprised in a detection region comprising the antigen, the antibody or an antigen-binding fragment thereof.

[8] The detection reagent according to the above [7], wherein the disaccharide is trehalose or maltose.

[9] The detection reagent according to the above [7] or [8], wherein the sugar alcohol is mannitol or sorbitol.

[10] The detection reagent according to any one of the above [7] to [9], which is an immunochromatography reagent.

[11] The detection reagent according to any one of the above [7] to [10], wherein the antibody or an antigen-binding fragment thereof is an anti-RS virus N protein antibody or an antigen-binding fragment thereof.

[12] A method for producing a detection reagent with increased detection sensitivity, in which an antigen, an antibody or an antigen-binding fragment thereof are immobilized, wherein disaccharide and sugar alcohol are added to a solution comprising an antigen, an antibody or an antigen-binding fragment thereof, and the antigen, the antibody or an antigen-binding fragment thereof are immobilized.

[13] The production method according to the above [12], wherein 1% to 4% (w/v) of the disaccharide and 0.5% to 4% (w/v) of the sugar alcohol are added to the solution comprising an antigen, an antibody or an antigen-binding fragment thereof, and the antigen, the antibody or an antigen-binding fragment thereof are immobilized on a carrier.

[14] The production method according to the above [12] or [13], wherein the disaccharide is trehalose or maltose.

[15] The production method according to any one of the above [12] to [14], wherein the sugar alcohol is mannitol or sorbitol.

[16] The production method according to any one of the above [12] to [15], wherein the detection reagent is an immunochromatography reagent.

[17] The production method according to any one of the above [12] to [16], wherein the antibody or an antigen-binding fragment thereof is an anti-RS virus N protein antibody or an antigen-binding fragment thereof.

The present description includes the contents as disclosed in Japanese Patent Application No. 2019-224865, which is a priority document of the present application.

Advantageous Effects of Invention

According to the method of the present invention, a carrier on which an antigen, an antibody or an antigen-binding fragment thereof is immobilized with adding disaccharide and sugar alcohol to a solution comprising an antigen, an antibody or an antigen-binding fragment thereof is used in immunoassay. Thus, the present method provides high sensitivity. In addition, according to the present invention, an immunoassay apparatus used in a novel detection method of the present invention is provided.

DESCRIPTION OF EMBODIMENTS

The present invention relates to an immunoassay method for detecting an analyte, wherein the method comprises immobilizing an antigen, an antibody or an antigen-binding fragment thereof on a carrier, then capturing the protein as an analyte by the immobilized carrier, and then detecting the captured protein as an analyte.

Examples of the analyte detected by the method of the present invention may include, but are not limited to: viral antigens, such as influenza virus antigen, adenovirus antigen, RS virus antigen, HA antigen, HBc antigen, HCV antigen, HIV antigen, EBV antigen, and NLV antigen; bacterial antigens, such as *Chlamydia trachomatis* antigen, *streptococcus* antigen, *Bordetella pertussis* antigen, *Helicobacter pylori* antigen, Leptospirosis antigen, *Treponema pallidum* antigen, *Toxoplasma gondii* antigen, *Borrelia* antigen, Anthrax antigen, and MRSA antigen; peptide hormones such as *Mycoplasma* lipid antigen and human chorionic gonadotropin; steroids such as steroid hormone; physiologically active amines, such as epinephrine and morphine; vitamins such as vitamin B; antibiotics, such as prostaglandins and tetracycline; toxins produced by bacteria, etc.; various types of tumor markers; agricultural chemicals; and anti-*E. coli* antibody, anti-*salmonella* antibody, anti-staphylococcal antibody, anti-*Campylobacter* antibody, anti-*Clostridium perfringens* antibody, anti-*Vibrio parahaemolyticus* antibody, anti-velotoxin antibody, anti-human transferrin antibody, anti-human albumin antibody, anti-human immunoglobulin antibody, anti-microglobulin antibody, anti-CRP antibody, anti-troponin antibody, anti-HCG antibody, anti-*Chlamydia trachomatis* antibody, anti-streptolysin O antibody, anti-*Helicobacter pylori* antibody, anti-β-glucan antibody, anti-HBe antibody, anti-HBs antibody, anti-adenovirus antibody, anti-HIV antibody, anti-rotavirus antibody, anti-influenza virus antibody, anti-parvovirus antibody, anti-RS virus antibody, anti-RF antibody, and nucleotides complementary to nucleic acid components derived from pathogenic microbes.

Hereinafter, the case of an RS virus used as an analyte will be described.

When the analyte is, for example, an RS virus, an anti-RS virus antibody is used as an antibody or an antigen-binding fragment thereof.

In the present invention, the anti-RS virus antibody is an antibody that specifically recognizes an RS virus, and specifically, the anti-RS virus antibody specifically recognizes the protein of the RS virus as an antigen and binds thereto. Examples of the protein of the RS virus may include F protein and N protein, which are associated with cell fusion. N protein is also referred to as "nucleoprotein," which consists of 391 amino acid residues. N protein is a structural component of a ribonucleoprotein complex, which is referred to as "nucleocapsid." N protein surrounds the genomic RNA of the RS virus and forms a spiral structure. Preferably, an antibody against the RS virus N protein is used.

In the present invention, when an anti-RS virus antibody is immobilized on a carrier, disaccharide and sugar alcohol are added, so that sensitivity to detect the RS virus can be improved.

Examples of the disaccharide may include trehalose and maltose.

Examples of the sugar alcohol may include mannitol and sorbitol.

Disaccharide and sugar alcohol may be added to an anti-RS virus antibody solution used in the immobilization. The anti-RS virus antibody solution is produced by dissolving the antibody in a buffer solution such as a phosphate buffer solution or a phosphate-buffered saline (PBS). At this time, the antibody concentration is several tens of pg/mL to several g/mL. The disaccharide concentration is 0.5% to 10% (w/v), preferably 1% to 5% (w/v), more preferably 1% to 4% (w/v), and particularly preferably 1% to 3% (w/v). The sugar alcohol concentration is 0.2% to 10% (w/v), preferably 0.5% to 5% (w/v), more preferably 0.5% to 4% (w/v), and particularly preferably 0.5% to 3% (w/v). These solutions may be, for example, linearly applied onto a carrier, and may be then dried.

Disaccharide and sugar alcohol are added to the antibody solution, followed by immobilization. Thereby, the sensitivity to detect the RS virus antigen is increased by 1.5 times or more, preferably by 1.75 times or more, and more preferably 2 times or more, in comparison to the case of not adding such disaccharide and sugar alcohol.

In the present invention, an antigen-binding fragment formed by separating only an antigen-binding site from the anti-RS virus antibody can also be used in the method of the present invention. That is to say, when fragments having specific antigen-binding ability (antigen-binding fragments), which are produced by known methods, such as Fab, Fab', F(ab')2, a single-chain antibody (scFv), dsFv, a diabody, and a minibody, are used, these fragments are encompassed in the present monoclonal antibody and are included in the scope of the present invention. In addition, the class of the monoclonal antibody is not limited to IgG, and may also be IgM or IgY.

The monoclonal antibody used in the method of the present invention can be obtained by immunizing an animal to be immunized with a complex or extract containing an antigen of interest, or an antigen or a partial peptide thereof according to a known immunological method, and then producing hybridomas using the cells of the immunized animal. The length of the peptide used in immunization is not particularly limited, and a peptide consisting of preferably 5 or more amino acids, and more preferably 10 or more amino acids can be used as an immunogen. Such an immunogen can be obtained from a culture solution, but it can also be obtained by incorporating DNA encoding any given antigen into a plasmid vector and then introducing the vector into host cells, so that it can be expressed therein. Any given antigen used as an immunogen or a partial peptide thereof is expressed as a fusion protein that is fused with any of the below-exemplified proteins, and it can be used as an immunogen, after purification or in an unpurified state. For the production of fusion proteins, there can be utilized glutathione S-transferase (GST), maltose-binding protein (MBP), thioredoxin (TRX), Nus tag, S tag, HSV tag, FRAG tag, polyhistidine tag, etc., which are commonly used as "protein expression/purification tags" by those skilled in the art. The fusion protein fused with any of these proteins is preferably used as an immunogen, after any given antigen or a partial peptide portion thereof has been separated from other tag portions by using a digestive enzyme, and has been then purified.

A monoclonal antibody can be easily prepared from an immunized animal according to a publicly-known method of Kohler et al. (Kohler et al., Nature, vol. 256, pp. 495-497 (1975)). Specifically, antibody-producing cells such as spleen cells or lymphocytes are recovered from an immunized animal, and the recovered cells are then fused with mouse myeloma cells according to an ordinary method to produce hybridomas. The obtained hybridomas are cloned by a limiting dilution method, etc., and thereafter, among monoclonal antibodies produced from the cloned hybridomas, a monoclonal antibody having an antigen-antibody reaction with an antigen used in the immunization of the animal is selected.

A monoclonal antibody can be purified from an ascitic fluid or a culture supernatant according to a known immunoglobulin purification method. Examples of the known immunoglobulin purification method may include a fractionation method according to salting-out using ammonium sulfate or sodium sulfate, a PEG fractionation method, an ethanol fractionation method, a DEAE ion exchange chromatography method, and a gel filtration method. Moreover, the monoclonal antibody can also be purified by an affinity chromatography method using a carrier binding to any of Protein A, Protein G, and Protein L, depending on the species of the immunized animal and the class of the monoclonal antibody.

According to the immunoassay method of the present invention, a measurement is carried out by an immunoassay that utilizes the antigen-antibody reaction of the monoclonal antibody produced as described above or an antigen-binding fragment thereof (hereinafter, in the description until before Examples, the term "antibody" means "an antibody or an antigen-binding fragment thereof," except for the case where it is clearly not the case from the context) with an antigen contained in a specimen. As an immunoassay method applied in the measurement, any of methods publicly known to those skilled in the art, such as a competitive method, an agglutination method, a Western blot method, an immunostaining method, and a sandwich method, can be applied. Besides, in the present invention, the term "measurement" includes any of quantification, semi-quantification, and detection.

The immunoassay is preferably a sandwich method. In the sandwich method, an antigen is sandwiched between two antibodies to form a complex, and the formed complex is detected. The sandwich method itself is publicly known in the field of immunoassay, and this method can be performed, for example, according to an immunochromatography method or an ELISA method. Both of these sandwich methods are publicly known, and the method of the present invention can be carried out according to such a publicly known sandwich method, except for the use of the above-described monoclonal antibody that recognizes the N protein as an antigen.

In the sandwich method, one or two or more types of antibodies that recognize an antigen (an antibody to be immobilized on a solid phase and a labeled antibody) are used. In the case of using two or more types of antibodies, at least any one of these two types of antibodies is the above-described monoclonal antibody that recognizes the N protein as an antigen. Otherwise, an antigen may be sandwiched between two antibodies of the same type to form a complex.

In an immunoassay involving a sandwich method as a detection principle, as a solid phase on which the antibody is immobilized, all of those capable of immobilizing the antibody thereon according to a known technique can be used. For example, a known solid phase, such as a porous thin membrane (membrane) having capillary action, a particulate substance, a test tube, or a resin flat plate, can be arbitrarily selected. In addition, as a substance that labels the antibody, an enzyme, a radioisotope, a fluorescent substance, a luminescent substance, a colored particle, a colloidal particle, etc. can be used. From the viewpoint of, in particular, the simplicity and rapidity of a clinical test, among the aforementioned immunoassay methods using various materials, immunochromatography, which is a lateral flow immunoassay method using a membrane, is preferable.

In the present invention, the present inventors also provide an immunoassay apparatus, which can perform a lateral flow immunoassay capable of improving sensitivity to detect an RS virus, by addition of disaccharide and sugar alcohol upon immobilization of an anti-RS virus antibody. The immunoassay apparatus provided by the present invention consists of: a carrier having a detection region, on which an antibody for capturing an analyte (an antigen) (Antibody 1) is immobilized; a label region having a movable labeled antibody (Antibody 2); a sample pad for adding dropwise a specimen; an absorption band for absorbing the spread specimen solution, and a backing sheet for adhering these members to one another. This is the immunoassay apparatus, in which at least either Antibody 1 or Antibody 2 is the monoclonal antibody recognizing the N protein as an antigen of the present invention. This immunoassay apparatus is also referred to as an "immunochromatography test piece."

The carrier is a material having an ability to immobilize an antibody for capturing a substance to be detected (an antigen), and the carrier also has an ability not to prevent the moving of a liquid in the horizontal direction. Preferably, the carrier is a porous thin membrane having capillary action, which is capable of transporting a liquid and a component dispersed in the liquid due to absorption. The material used for the carrier is not particularly limited, and examples of the material of the carrier may include cellulose, nitrocellulose, cellulose acetate, polyvinylidene difluoride (PVDF), glass fiber, nylon, and polyketone. Among these materials, a thin membrane formed using nitrocellulose is more preferable. A membrane, on which the antibody is immobilized, is referred to as an "antibody-immobilized membrane."

The label region consists of a porous base material comprising a labeled antibody, and as a material used for the base material, commonly used glass fiber, non-woven fabric, etc. can be used. For impregnation with a large amount of labeled antibody, the base material is preferably a pad-shaped material having a thickness of approximately 0.3 mm to 0.6 mm. The porous base material that is impregnated with the labeled antibody and is then dried is also referred to as a "dry pad."

For labeling a labeled antibody, enzymes such as alkaline phosphatase or horseradish peroxidase, metal colloids such as gold colloids, silica particles, cellulose particles, colored polystyrene particles, colored latex particles, etc. are used in many cases. In the case of using metal colloidal particles, or colored particles such as colored polystyrene particles or colored latex particles, since coloration is generated as a result of agglutination of these labeling reagents, this coloration is measured. Particles, on which the antibodies are immobilized, are referred to as "antibody-immobilized particles." The amount of the antibody immobilized is not particularly limited, and it is adequate if the antibody may be present in the label region in an amount of several ng to several tens of µg.

The detection region indicates a partial region of the carrier, on which an antibody for capturing a substance to be detected (an antigen) is immobilized. In the detection region, at least one region, on which an antibody for capturing an antigen is immobilized, is established. The detection region may be included in the carrier, and an antibody may be immobilized on the carrier. As described above, when the anti-RS virus antibody is immobilized on the detection region, disaccharide and sugar alcohol are added into the anti-RS virus antibody solution. The amount of the antibody immobilized is not particularly limited, and it is adequate if the antibody may be immobilized on the detection region in an amount of several ng to several tens of μg. The detection region of the present invention detectably comprises disaccharide and sugar alcohol.

The sample pad is a site to which a specimen is adding dropwise, and is a porous material. The sample pad is a site located most upstream of the immunoassay apparatus. As a material used for the sample pad, commonly used filter, glass fiber, non-woven fabric, etc. can be used. In order to use a large amount of specimen in the immunoassay, the sample pad is preferably a pad-shaped material having a thickness of approximately 0.3 mm to 1 mm. Examples of the specimen may also include a sample or the like that is obtained by allowing the specimen to float in another solution, and a sample prepared using the specimen.

The absorption band is a member for absorbing a component that is supplied to the carrier and is not involved in the reaction in the detection region. As a material used for the absorption band, a water-retentive filter, sponge, etc. consisting of a common natural polymer compound or synthetic polymer compound, etc. can be used. In order to promote the developing of the specimen, a material having a high water absorption rate is preferable.

The backing sheet is a member for adhering all of the aforementioned materials, namely, a carrier, a sample pad, a label region, an absorption band and the like, to one another, with partial overlapping, and for immobilizing them. The backing sheet is not always necessary, if these materials are disposed and immobilized with optimal intervals. However, for the convenience of production or use, it is generally preferable to use the backing sheet.

The immunoassay apparatus of the present invention may further comprise a control display region (a member). The control display region is a site for showing that the test has been accurately carried out. For example, the control display region is located downstream of the detection region, and emits signals such as coloration, when a specimen sample passes through the detection region and reaches the control display region. On the control display region, a substance that binds to an antibody binding to a labeled carrier may be immobilized, or a reagent, such as a pH indicator whose color is changed when the specimen reaches, may be immobilized. When such a labeled carrier-binding antibody is a mouse monoclonal antibody, an anti-mouse IgG antibody may be used.

The size of the immunoassay apparatus is not limited. For example, the present immunoassay apparatus has a vertical length of several cm to some dozen cm, and a horizontal length of several mm to several cm.

The immunoassay apparatus of the present invention may be placed in a containment cassette (vessel). By using this containment cassette, deterioration of the immunoassay apparatus due to, for example, ultraviolet ray or moisture in the air, can be prevented. Moreover, in the case of using a specimen sample having contamination or infectivity, by using the containment cassette, a tester who performs an assay can be prevented from being contaminated or infected. For example, a resin case having an appropriate size may be used as a containment cassette, and the apparatus of the present invention may be placed in the case. The containment cassette and the immunoassay apparatus placed in the cassette are collectively referred to as an "immunoassay device" in some cases.

An RS virus detection reagent containing the anti-RS virus N protein monoclonal antibody of the present invention comprises the above-described immunoassay apparatus. In addition, an RS virus detection kit containing the anti-RS virus N protein monoclonal antibody of the present invention comprises the above-described immunoassay apparatus. The kit may further comprise a brochure, a specimen-collecting device, etc.

According to the present method, utilizing capillary action, a complex of: Antibody 2 capable of binding to a substance to be detected (a labeling reagent), which has been labeled with a suitable labeling substance such as a colored polystyrene particle or a gold colloid; and the substance to be detected, is developed and moved to a solid-phase carrier, on which Antibody 1 is immobilized. As a result, a complex consisting of an immobilized substance, a substance to be detected, and a labeling reagent is formed on the solid-phase carrier, and the signals of the labeling reagent emitted from the complex are then detected (in the case of using a gold colloid, the solid-phase carrier portion, on which the substance capable of binding to the substance to be detected is immobilized, becomes red), so that the substance to be detected can be detected. This immunoassay method can be carried out at a temperature of 5° C. to 35° C., and preferably at room temperature.

According to the method of the present invention, whether or not a subject is infected with an RS virus can be detected. When an N protein is detected in the sample of a subject, the subject can be determined to be infected with an RS virus.

When the antibody recognizing an N protein of the present invention is used, an RS virus can be specifically recognized. The antibody recognizing an N protein does not recognize other viruses such as, for example, Adenovirus, Coxsackievirus, Echo virus, Herpes simplex virus, Human Metapneumovirus, Influenza virus, Measles virus, Mumps virus, and Parainfluenza virus, and thus, the antibody recognizing an N protein does not falsely detect these viruses.

Moreover, even clinically isolated strains, which cannot be detected by using the antibody that recognizes the F protein of an RS virus, can be detected by using the antibody recognizing the N protein of an RS virus of the present invention.

Examples of the specimen sample used herein may include specimens such as pharyngeal or nasal cavity swab, pharyngeal or nasal cavity lavage fluid, nasal cavity aspirate fluid, saliva, serum, rectal swab, feces, feces suspension, urine, and cornea swab.

EXAMPLES

Hereinafter, the present invention will be more specifically described based on the following examples. However, the following examples are not intended to limit the scope of the present invention.

Example 1: Production of Anti-RS Virus N Protein Monoclonal Antibody

1. Preparation of RS Virus N Protein Antigen

RS virus-sensitive mammalian cells were infected with the RS virus, and were then cultured for several days. Thereafter, a culture solution of the RS virus-infected cells was inactivated by ultraviolet irradiation, and was then used.

2. Production of RS Virus N Protein Monoclonal Antibody

BALB/c mice were immunized with the RS virus-inactivated antigen prepared in the above 1., and were then bred for a certain period of time. Thereafter, the iliac lymph node was excised from each mouse. According to such "mouse iliac lymph node method" (Sado Y et al., Acta Histochem. Cytochem. 39: 89-94 (2006)), a plurality of hybridoma cell lines producing anti-RS virus N protein antibodies were obtained.

The thus obtained cell line was intraperitoneally administered into a pristane-treated BALB/c mouse, and approximately 2 weeks after the administration, an antibody-containing ascitic fluid was collected. From the obtained ascitic fluid, IgG was purified by an affinity chromatography method using a Protein A column, and a plurality of purified anti-RS virus N protein monoclonal antibodies (hereinafter referred to as "anti-N protein antibodies" at times) were obtained.

In the following examples, taking into consideration reactivity and specificity, antibodies were selected from the obtained plurality of anti-RS virus N protein monoclonal antibodies, and were then used.

Example 2: Immunoassay Apparatus for Measuring RS Virus

1. Immobilization of Anti-RS Virus N Protein Antibody on Nitrocellulose Membrane

A solution prepared by diluting the anti-N protein antibody produced in Example 1 with a buffer solution, and an anti-mouse IgG antibody were prepared. Thereafter, the anti-N protein antibody was linearly applied onto the sample pad side of a nitrocellulose membrane backed with a PET film, and the anti-mouse IgG antibody was linearly applied onto the absorbent side thereof. Thereafter, the nitrocellulose membrane was fully dried with warm air, so as to obtain an anti-N protein antibody-immobilized membrane.

2. Immobilization of Anti-RS Virus N Protein Antibody on Colored Polystyrene Particles

The anti-N protein antibody produced in Example 1 was covalently bound to colored polystyrene particles, and the resultant was suspended in a floating liquid and was fully dispersed therein by an ultrasonic treatment, so as to obtain anti-N protein antibody-binding colored polystyrene particles. In the present description, the anti-N protein antibody-binding colored polystyrene particles are referred to as "anti-N protein antibody-immobilized particles."

3. Application of Anti-RS Virus N Protein Antibody-Binding Colored Polystyrene Particles and Drying Thereof

The antibody-immobilized particles produced in the above 2. were applied in a predetermined amount onto a glass fiber non-woven fabric, and were then fully dried with warm air. In the present description, the thus obtained product is referred to as a "labeling pad."

4. Production of RS Virus-Testing Device

The antibody-immobilized membrane produced in the above 1., the labeling pad produced in the above 2. and 3., and other members (a backing sheet, an absorption band, and a sample pad) were adhered to one another, and the obtained product was then cut to a width of 5 mm, thereby obtaining an RS virus-testing device.

5. Confirmation of Specificity and Accuracy of RS Virus-Testing Device

A specimen floating liquid (50 μL) containing a virus causing respiratory tract infection (10 mM Tris (pH 8.0), 1% (w/v) polyoxyethylene octyl phenyl ether, 3% (w/v) arginine, and 3% (w/v) BSA) was added dropwise onto the RS virus-testing device produced in the above 4., and was then left at rest for 5 minutes.

When coloration could be confirmed by visual observation at the positions, onto which both the anti-mouse IgG antibody and the anti-N protein antibody had been applied, it is determined to be +. When coloration could be confirmed by visual observation only at the position, onto which the anti-mouse IgG antibody had been applied but the coloration could not be confirmed at the position, onto which the anti-N protein antibody had been applied, it is determined to be −. Moreover, when coloration could not be confirmed by visual observation at the position, onto which the anti-mouse IgG antibody had been applied, it is determined to be invalid.

The results are shown in Table 1.

TABLE 1

| Virus name | Measurement results |
| --- | --- |
| RS virus Long strain (type A) | + |
| RS virus A-2 strain (type A) | + |
| RS virus CH-18 strain (type B) | + |
| Adenovirus type 1 | − |
| Adenovirus type 2 | − |
| Adenovirus type 3 | − |
| Adenovirus type 4 | − |
| Adenovirus type 5 | − |
| Adenovirus type 7 | − |
| Adenovirus type 19 | − |
| Coxsackievirus type A9 | − |
| Coxsackievirus type B4 | − |
| Coxsackievirus type B5 | − |
| Coxsackievirus type B6 | − |
| Echo virus type 2 | − |
| Echo virus type 3 | − |
| Echo virus type 4 | − |
| Echo virus type 6 | − |
| Echo virus type 9 | − |
| Echo virus type 11 | − |
| Echo virus type 30 | − |
| Herpes simplex virus type 1 | − |
| Human Metapneumovirus type A | − |
| Human Metapneumovirus type B | − |
| Influenza virus A/New Caledonia/20/99 (H1N1) | − |
| Influenza virus A/Beijing/262/95 (H1N1) | − |
| Influenza virus A/New York/55/2004 (H3N2) | − |
| Influenza virus A/Hiroshima/52/2005 (H3N2) | − |
| Influenza virus B/Shanghai/361/2002 (Yamagata) | − |
| Influenza virus B/Malaysia/2506/2004 (Victoria) | − |
| Measles virus | − |
| Mumps virus | − |
| Parainfluenza virus type 1 | − |
| Parainfluenza virus type 2 | − |
| Parainfluenza virus type 3 | − |
| Parainfluenza virus type 4 | − |

As shown in Table 1, the immunoassay apparatus using the anti-RS virus N protein antibody of the present invention reacts with the RS virus, but does not exhibit cross-reactivity with other respiratory tract infection-causing viruses. Accordingly, it could be confirmed that the anti-RS virus N protein antibody of the present invention specifically reacts with the RS virus.

Example 3: Highly-Sensitive RS Virus-Testing Device Using Anti-RS Virus N Protein Monoclonal Antibody It was confirmed that the RS virus-testing device, in which the anti-N protein antibody produced by Example 2 was used, had lower sensitivity to detect the RS virus antigen than a test device produced using an anti-RS virus F protein monoclonal antibody (an anti-F protein antibody).

When the anti-N protein antibody was immobilized on a nitrocellulose membrane in Example 2-1., disaccharide and sugar alcohol were added, so that the detection sensitivity equivalent to that of the test device using the anti-F protein antibody could be obtained.

1. Production of Highly-Sensitive Anti-N Protein Antibody-Immobilized Membrane

Upon the immobilization of the anti-N protein antibody in Example 2-1., 2% (w/v) of trehalose was added as disaccharide to the buffer solution, and 1.0% to 2.0% (w/v) of mannitol was further added. The thus obtained mixture was linearly applied onto a nitrocellulose membrane, and the nitrocellulose membrane was then fully dried with warm air, so as to obtain a highly-sensitive anti-N protein antibody-immobilized membrane.

2. Evaluation of Highly-Sensitive Anti-N Protein Antibody-Immobilized Membrane

Using the highly-sensitive anti-N protein antibody-immobilized membrane, an RS virus-testing device was prepared according to the method described in Example 2-4. Then, using a 2-fold dilution series solution of the RS virus antigen, the test was carried out according to the method described in Example 2-5. The results are shown in Table 2.

When coloration could be confirmed by visual observation at the positions, onto which both the anti-mouse IgG antibody and the anti-N protein antibody had been applied, it is determined to be +. When coloration could be confirmed by visual observation only at the position, onto which the anti-mouse IgG antibody had been applied, but the coloration could not be confirmed at the position, onto which the anti-N protein antibody had been applied, it is determined to be −. Moreover, when coloration could not be confirmed by visual observation at the position, onto which the anti-mouse IgG antibody had been applied, it is determined to be invalid.

TABLE 2

| Additive amount of mannitol | RS virus antigen dilution ratio | | | |
|---|---|---|---|---|
| | 2 | 4 | 8 | 16 |
| Non | + | − | − | − |
| 1.0% | + | + | − | − |
| 2.0% | + | + | − | − |

It was confirmed that the sensitivity was two-fold increased by addition of disaccharide and mannitol.

INDUSTRIAL APPLICABILITY

Using the antibody of the present invention, RS virus infection can be specifically detected with high sensitivity.

All publications, patents and patent applications cited in the present description are incorporated herein by reference in their entirety.

The invention claimed is:

1. A method for detecting RS virus N protein in a specimen sample by immunochromatography, comprising
contacting the specimen sample with an anti-RS virus N protein antibody or an antigen-binding fragment thereof,
wherein the anti-RS virus N protein antibody or an antigen-binding fragment thereof is immobilized to a carrier by adding trehalose and mannitol to a solution comprising the anti-RS virus N protein antibody or antigen-binding fragment thereof, and
wherein detection sensitivity is increased relative to that achieved in the absence of trehalose and mannitol.

2. The method according to claim 1, wherein 1% to 4% (w/v) of trehalose and 0.5% to 4% (w/v) of mannitol are added to the solution comprising the anti-RS virus N protein antibody or antigen-binding fragment thereof, so that the anti-RS virus N protein antibody or antigen-binding fragment thereof is immobilized on the carrier.

3. An RS virus N protein detection reagent comprising an immobilized anti-RS virus N protein antibody or an antigen-binding fragment thereof,
wherein the detection reagent is an immunochromatography test piece,
wherein trehalose and mannitol are comprised in a detection region comprising the anti-RS virus N protein antibody or antigen-binding fragment thereof, and
wherein detection sensitivity of the detection reagent is increased relative to that achieved in the absence of trehalose and mannitol.

4. A method for producing an RS virus N protein detection reagent, comprising
contacting a solution comprising an anti-RS virus N protein antibody or antigen-binding fragment thereof with trehalose and mannitol, thereby immobilizing the anti-RS virus N protein antibody or antigen-binding fragment thereof,
wherein the detection reagent is an immunochromatography test piece, and
wherein the detection reagent has increased detection sensitivity relative to that achieved in the absence of trehalose and mannitol.

5. The method according to claim 4, wherein 1% to 4% (w/v) of trehalose and 0.5% to 4% (w/v) of mannitol are added to the solution comprising the anti-RS virus N protein antibody or antigen-binding fragment thereof, and the anti-RS virus N protein antibody or antigen-binding fragment thereof is immobilized on a carrier.

* * * * *